(12) United States Patent
Reuter et al.

(10) Patent No.: US 9,636,081 B2
(45) Date of Patent: May 2, 2017

(54) METHOD AND APPARATUS FOR RECOGNIZING MOVING ANATOMICAL STRUCTURES USING ULTRASOUND

(75) Inventors: Stefan Reuter, Stuttgart (DE); Alexander Dubielczyk, Stuttgart (DE); Markus Wohlschlager, Sindelfingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 268 days.

(21) Appl. No.: 13/376,968

(22) PCT Filed: Jun. 7, 2010

(86) PCT No.: PCT/IB2010/052506
§ 371 (c)(1),
(2), (4) Date: Dec. 8, 2011

(87) PCT Pub. No.: WO2010/143113
PCT Pub. Date: Dec. 16, 2010

(65) Prior Publication Data
US 2012/0083699 A1    Apr. 5, 2012

(30) Foreign Application Priority Data
Jun. 9, 2009 (EP) .................... 09162259

(51) Int. Cl.
*A61B 8/02*     (2006.01)
*A61B 5/024*    (2006.01)
(Continued)

(52) U.S. Cl.
CPC ............ *A61B 8/02* (2013.01); *A61B 5/02411* (2013.01); *A61B 5/4362* (2013.01);
(Continued)

(58) Field of Classification Search
CPC . A61B 5/02411; A61B 5/4362; A61B 5/7257; A61B 5/7264; A61B 5/7267; A61B 8/02; A61B 8/0866; A61B 8/488
(Continued)

(56) References Cited

U.S. PATENT DOCUMENTS 4,299,234 A  * 11/1981 Epstein et al. ............... 600/511
4,770,184 A    9/1988  Greene
(Continued)

FOREIGN PATENT DOCUMENTS

FR    2602413 A1    2/1988

OTHER PUBLICATIONS

Georgoulas, George G. et al "Classification of Fetal Heart Rate during Labour using Hidden Markov Models" Neural Networks, 2004, Proceedings IEEE International Joint Conference. vol. 3, pp. 2471-2475.
(Continued)

*Primary Examiner* — Katherine Fernandez

(57) ABSTRACT

A method of recognizing at least one moving anatomical structure using ultrasound data that operates by receiving ultrasound data (100). The ultrasound data comprises Doppler shift information which provides information descriptive of the velocity of at least one anatomical structure. The ultrasound data is first divided into a series of time frames (102). A classification is then assigned to each of the time frames using the Doppler shift information (104). The at least one anatomical structure is then recognized by using the classification of each time frame (106). This is possible, because different anatomical structures produce different patterns in the Doppler shift information.

16 Claims, 4 Drawing Sheets

(51) Int. Cl.
*A61B 5/00* (2006.01)
*A61B 8/08* (2006.01)

(52) U.S. Cl.
CPC .......... *A61B 5/7264* (2013.01); *A61B 8/0866* (2013.01); *A61B 8/488* (2013.01); *A61B 5/7257* (2013.01); *A61B 5/7267* (2013.01)

(58) Field of Classification Search
USPC .......................... 600/438, 450, 453; 382/128
See application file for complete search history.

(56) References Cited

U.S. PATENT DOCUMENTS

| | | | |
|---|---|---|---|
| 4,984,574 A * | 1/1991 | Goldberg et al. | 600/410 |
| 5,494,032 A * | 2/1996 | Robinson et al. | 600/323 |
| 6,093,151 A * | 7/2000 | Shine et al. | 600/485 |
| 6,254,537 B1 | 7/2001 | Nguyen | |
| 6,751,498 B1 | 6/2004 | Greenberg | |
| 2005/0015009 A1 | 1/2005 | Mourad | |
| 2005/0251044 A1 * | 11/2005 | Hoctor et al. | 600/444 |
| 2007/0027396 A1 | 2/2007 | Assaleh | |
| 2007/0066908 A1 * | 3/2007 | Graupe et al. | 600/511 |
| 2007/0260154 A1 | 11/2007 | Rapoport | |

OTHER PUBLICATIONS

Ibrahimy, M.I. et al "Real-Time Signal Processing for Fetal Heart Rate Monitoring" IEEE Transactions on Biomedical Engineering, vol. 50., No. 2, Feb. 2003, pp. 258-262.

Murray, Michelle L. "Maternal or Fetal Heart Rate? Avoiding Intrapartum Misidentification" Jognn Clinical Issues, vol. 33, No. 1, pp. 93-104.

\* cited by examiner

METHOD AND APPARATUS FOR RECOGNIZING MOVING ANATOMICAL STRUCTURES USING ULTRASOUND

FIELD OF THE INVENTION

The invention relates to ultrasound diagnostics of a subject, in particular for recognizing anatomical structures which generate Doppler shifts in an ultrasound signal.

BACKGROUND OF THE INVENTION

Fetal monitors are devices to detect and to record the fetal heart rate. However, in case of weak of absent fetal heart signs, or if transducers are incorrectly placed, they may unintentionally record the maternal heart rate. These maternal heart rate patterns can mimic fetal heart rate patterns on such recordings. As a result, lawsuits are filed every year involving cases in which health care providers failed to differentiate between maternal and fetal heart rate patterns. Misinterpreting a heart rate trace may lead to unnecessary actions, unnecessary surgery, delayed delivery of a compromised fetus, or even fetal death.

United States patent application publication US 2007/0066908 A1 describes a method and an apparatus by which one or more fetal heart components are separated from heart signal information obtained from a pregnant female based upon singular value decomposition.

SUMMARY OF THE INVENTION

The invention provides for a method of recognizing moving anatomical structures using ultrasound data a computer program product, a control system, and a fetal monitor in the independent claims. Embodiments of the invention are described in the dependent claims.

Embodiments of the invention address the aforementioned problem by performing a spectral decomposition of ultrasound data which contains Doppler shift velocity information. Different portions of a subject move at different rates. For instance when the heart moves, the heart wall and heart valves move at different velocities. In addition certain types of internal motion by a subject are cyclical or have specific patterns. Using the example of the heart, there is a certain pattern of heart chamber contractions (heart wall movement) and heart valve movements. A knowledge of or a model of these movements and their sequential order can be used to recognize what is being examined using the ultrasound transducer without the need for an imaging system. In the case of a heart, it allows the identification that the ultrasound transducer is placed correctly so that the fetal heart rate is detected.

Some embodiments of the invention use pattern recognition to identify different physiological signals sources and consequently provide a method to distinguish between maternal and fetal ultrasound signals. Thus the risk of trace misinterpretation can be minimized. Furthermore, the algorithm can also be used to classify different types of fetal movements and therefore provide additional information descriptive of the fetus' condition and wellbeing. The method does not require any additional cables or transducers or any other efforts, which is crucial for the method to be well accepted by caregivers and subjects.

Fetal monitors are defined as devices for measurement and visualization of more than one physiological parameter of unborn human beings. These monitors consist of multiple sensor elements for measuring uterine activity and the fetal heart beat. Basically, two methods are used for electronic monitoring:

The external or indirect method uses external transducers placed on the maternal abdomen. Typically, Ultrasound Doppler (US) transducers are used in this category, where high frequency sound waves reflect mechanical action of the fetal heart The internal or direct method uses a spiral electrode to derive the fetal electrocardiogram obtained from the presenting part of the unborn. This method can be used only when the presenting part is accessible and identifiable.

Fetal monitors use ultrasound Doppler technology for non-invasive acquisition and recording of the fetal heart rate during gestation and labor. The mechanical contraction for the fetal heart muscle leads to periodic signal patterns in the ultrasound reflection. The period of the patterns is used by fetal monitors to determine the fetus' current heart rate. A major issue of this technology is its indifference to the physiological signal source which generates the ultrasound reflection. All periodic movements of tissue or blood flow in range of the ultrasound beam can generate a heart rate within the fetal monitor. Pulsations of the mother's abdominal arteries are a well-known cause for this problem. In this case, fetal monitors sometimes misleadingly record the maternal, instead of fetal, heart rate.

Additionally, traces recorded with the ultrasound Doppler technology can show the phenomenon of double counting. Double counting may occur if a maternal aortic wall movement during systole is nearly identical to the aortic wall movement during diastole. The envelope wave derived from the sensor signal then has identical shapes and the fetal monitor software cannot detect a difference between the two. Instead of counting a beat of the heart as one, two will be counted which can double the heart rate. Therewith, hear rate doubling occasionally occurs when measuring weak signals caused, for example, by aortic wall movements. Often the doubled maternal heart rate appears to have exaggerated variability and therefore may be interpreted as a fetal heart rate.

To help the caregiver recognize a false heart rate, modern fetal monitors offer to synchronously measure the mother's heart rate via ECG or pulse oximetry. If the maternal heart rate matches the heart rate measured via the ultrasound sensor, the monitor alerts the caregiver. However, these methods are not able to distinguish between fetal and maternal heart rate. They can only alarm the caregiver if the two recorded heart rates are identical, saying that there is a high probability that the source of the ultrasound signal may be in fact a maternal anatomical structure. These methods require either additional sensors, or at least additional electrodes, to derive the maternal heart rate. Electrodes and sensors add additional cables, thus increasing subject and caregiver inconvenience. As a result, any method that adds additional sensors or electrodes is not well accepted.

Some embodiments of the invention differentiate physiological signal sources by modeling characteristic signal patterns for each source. Ultrasound signal sequences are therefore compared with models of known sources and classified by the best fitting model. When the source of the ultrasound signal is known, the fetal monitor can display this information on its screen, or simply notify the caregiver if the signal source is any other than the fetal heart. Furthermore, the modeling of movement patterns can be used to detect pathological conditions of the fetal heart or measure the duration of some mechanical events in the fetal heart cycle. This information provides further possibilities for a more detailed diagnosis by the responsible caregiver.

The same method can be used to classify different types of fetal movements. With the new algorithm, it is possible to distinguish between different types of fetal movements, e.g. breathing, sucking, or moving the arms and legs.

Some embodiments of the invention can be constructed by the integration of a pattern recognition algorithm into the ultra sound signal processing of the fetal monitor. This algorithm can differentiate between fetal and maternal ultrasound signals. With this pattern recognition algorithm, the fetal monitor can determine the physiological source of the ultrasound signal. This determination is possible because the fetal heart, as well as the pulsation of the umbilical cord, fetal movements or pulsating maternal vessels, all have a unique ultrasound pattern "fingerprint" that can be modeled, for example, by Hidden Markov Models (HMMs). HMMs are multi parameter models that can classify the ultrasound signals by numerous characteristics, such as alignment of sub patterns during on heartbeat (e.g. heart valve movement) and myocardium movement), their individual duration, occurrence and frequency, as well as the signal's energy or its spectral composition. The combination of all these characteristics is unique for each physiological source.

Embodiments of the invention function by dividing the ultrasound data into shorter time frames. Each of the time frames is classified and then patterns in the classification are used to identify the anatomical structure that is generating the Doppler shift information in the ultrasound signal. Looking at the patterns of the classifications is crucial, because on a short time scale noise and artifacts in the ultrasound data can make it unclear as to what is the source of the Doppler shifts. When a pattern for a longer time period is examined then a more accurate conclusion as to which anatomical structure is generating the Doppler shift emerges.

A single event that can be seen in the Doppler shift spectrum could be part of a physiological signal, but it also could be caused by an artifact. An isolated event that isolated looks similar to e.g. a heart valve reflection could also be a body or transducer movement. It's very important, that we can only say something reliable about the anatomical source when a full time frame is examined. In the case of fetal heart identification this would be one or two heart beats. By looking on the whole sequence of single events makes it possible to say something about the signal source. When we have the whole sequence of single events in a time frame we can say whether it's likely that the whole pattern it is produced by, for example, a fetal heart cycle. HMMs are very good at this type of pattern recognition.

Additionally, embodiments of the invention may provide further diagnostic information:

The time between single actions (e.g. heart valve movement and myocardium movement) as well as the duration of certain actions (e.g. systole and diastole) can be measured and may indicate pathological conditions. This additional information offers further possibilities for a reliable diagnosis and better treatment.

In some embodiments the invention may be incorporated into existing fetal monitors by integrating additional signal processing algorithms into the existing processor of the fetal monitoring device, thus the assembling for a standard fetal monitor (1 TOCO sensor, 1 ultrasound sensor) does not need to change. This ensures a simple integration into the clinical environment so that caregivers and midwives do not need any extra training.

Embodiments of the invention may have the following benefits:

The ultrasound pattern recognition algorithm can distinguish between different ultrasonic patterns and therefore distinguish between fetal and maternal sources, so unintentional measurement of maternal instead of the fetal heart rates may be ruled out, and the caregiver can be sure to record the fetal heart rate.

The method can be trained automatically with existing clinical signals. No lengthy manual adjustment is required. Additional patterns may also be added.

The caregiver can be sure to measure the fetal heart instead of, for example, the pulsating umbilical cord.

A simple visual or acoustical signal generated by the fetal monitor can alarm the caregiver.

Embodiments may identify certain single events in the acoustical signal. Therefore additional information (e.g. duration and occurrence of specific heart actions) can be derived from the signal thus allowing a more detailed diagnosis and better treatment and identification of pathological signal patterns.

It may identify different types of fetal movements.

Embodiments may provide an additional signal quality indicator.

Embodiments of the method can be integrated simply into the existing processor, so it is possible to easily upgrade the installed base.

No additional effort and no extra sensors or cables are required. Consequently there will be no decline of subject comfort.

No extra training of caregivers is necessary; therefore the acceptance in clinics will be high.

The cost of ownership does not change.

The reliability of fetal monitoring is significantly increased and the risk of intrapartum fetal mortality is reduced.

Increasing the robustness of the detection algorithm for fetal monitoring and avoiding fetal heart rate misinterpretation is crucial for the success of monitoring devices. The advantage of this invention is that the caregiver can be informed about which physiological structure is the source of the current acoustical signal. This enables the caregiver to be sure to monitor the fetal heart with the ultrasound sensor. Unintentional measurement of maternal structures will be detected and consequently signaled by the fetal monitor. Additionally, the new algorithm gives more information of the current signal source. It can indicate pathological patterns and provide more information for a more detailed diagnosis. To use this new feature, neither additional training nor any additional equipment is needed. This ensures that the acceptance in labor rooms by midwives and other caregivers will be high.

A labor contraction sensor is defined herein as a sensor used to measure contractions during labor. One example of a labor contraction sensor is known as a toco sensor. Examples of labor contraction sensors are sensors that measure labor contractions using a strain gauge, a microphone, piezo-electric materials, moving coils or by measuring the electrical signals generated by the body during the labor contractions.

A fetal monitor is a monitor that is capable of monitoring at least one parameter indicating the health of a fetus. Fetal monitors are typically capable of monitoring the heart rate of a fetus. Electrocardiography (ECG), Saturation of Peripheral Oxygen (SPO2), and/or Non-Invasive Blood Pressure (NIBP) sensors can also be used with many Fetal monitors to monitor maternal vital signs.

Ultrasound data is defined herein as the data obtained by an ultrasound system using an ultrasound transducer. An ultrasound system sends pulses of ultrasound into a tissue region using a transducer and measures the ultrasound that is reflected. The internal structure of a subject can be investigated. Doppler changes in the ultrasound signal can be used to determine the velocity of blood or internal structures within a subject.

Doppler shift information is defined herein as velocity information that is derived from ultrasound data.

Fetal heart valve motion data is defined herein as ultrasound data that indicates the motion of a fetal heart valve. Fetal heart wall motion data is defined herein as ultrasound data that indicates the motion a fetal heart wall.

A trained software module is defined herein as a pattern recognition module that can be trained using a set of training data. A pattern recognition module is defined herein as a software module adapted for recognizing patterns in data. A pattern recognition module can be implemented by using a variety of different methods. Examples of different methods or algorithms that could be used are: Principal Component Analysis, Neural Network, CN2 algorithm, C4.5 algorithm, Iterative Dichotomiser 3 (ID3), nearest neighbor search algorithm, naive Bayes classifier algorithm, Holographic Associative Memory, or perception learning algorithm. A pattern recognition algorithm is also referred to herein as a classification algorithm. The pattern recognition module may work by using a feature vector as input. Training data may be generated using exemplary feature vectors or may be constructed using simulated data or models.

The invention provides for a method of recognizing at least one anatomical structure using ultrasound data. The method comprises the step of receiving ultrasound data. The ultrasound data comprises Doppler shift information descriptive of the velocity of the at least one anatomical structure. The method comprises the step of dividing the ultrasound data into a series of time frames. The method comprises the step of assigning each of the time frames a classification using the Doppler shift information. The method comprises the step of recognizing the at least one anatomical structure using the classification of each time frame. This method has the advantage of being able to recognize which anatomical structure or structures is responsible for generating Doppler shifts in the ultrasound data even when the data contains noise and artifacts. This is accomplished by recognizing patterns of the classifications.

The timeframes are useful if they are divided into the order of approximately 10 milliseconds. Longer times and shorter times may also be used. Times in the range of 1 millisecond to 15 milliseconds are also useful. Classifying the fetal heart motion for each of the sequential frames is beneficial, because during a heart beat there is a regular sequence of events. For instance, the various heart valves and chambers open and close or contract and expand at a regular interval. This means that models can be developed which can be used to classify the fetal heart motion.

In another embodiment, the anatomical structure is recognized to be either fetal or maternal in origin. This is advantageous, because it prevents the maternal heart rate from being erroneously identified as being the fetal heart rate.

In another embodiment, the step of assigning each of the time frames a classification using the Doppler shift information comprises the steps of identifying fetal heart valve motion data using the Doppler shift information. The step of assigning each of the time frames a classification using the Doppler shift information further comprises the steps of identifying fetal heart wall motion data using the Doppler shift information. A fetal heart is then recognized as being one of the at least one anatomical structures using the classification of each of the time frames. This embodiment is advantageous, because fetal hearts generate a periodic pattern which can be recognized. The method prevents false identification of a maternal heart beat as the fetal one. The fetal heart has patterns of fast heart valve motion and slower heart wall motion which can be positively identified in the ultrasound data.

In another embodiment, the invention provides for a method of determining a fetal heart rate. The method further comprises the step of identifying fetal heart valve motion using the Doppler shift information. The method further comprises the step of identifying fetal heart wall motion data using the Doppler shift information. The method further comprises the step of identifying fetal heart wall motion data using the Doppler shift information. The method further comprises the step of determining the fetal heart rate using the heart valve motion data and the heart wall motion data. This embodiment is advantageous, because the fetal heart valve moves more rapidly than the fetal heart wall does. By identifying the fetal heart valve motion and the fetal heart wall motion one is able to recognize detectable patterns that indicate that the ultrasound system is in fact receiving ultrasound data which originates from a fetus. This method has the great advantage that a single sensor can be used to determine if the fetal heart rate is being measured or not. No external sensor to monitor the mother's heart rate independently is needed.

In another embodiment, the fetal heart rate is determined by comparing the pattern of fetal heart valve motion and heart wall motion in a Fourier transfer of the ultrasound data with a fetal heart model. As was mentioned before the heart valve motion is more rapid than the heart wall motion. This allows the two types of data to be separated in a Fourier transform.

In another embodiment, the step of assigning each of the time frames a classification using the Doppler shift information comprises the steps of identifying fetal body motion using the Doppler shift information. The anatomical structure is identified to be a fetal body using the classification of each of the time frames. Fetal body motion is defined herein as voluntary motion of the body of a fetus or motion of the body of a fetus which involves multiple organs and muscles. Examples would be moving limbs, moving its head, sucking a thumb, or hiccupping. Fetal body motion can be identified, because the fetal motions are longer than that of the heart rate. Fetal motions will typically be of the order of half a second to several seconds. In addition, fetal body motion is not rapid. The Doppler shifts of fetal body motion will typically be below 10 Hz. When the fetus moves, a large region is moving, so the amplitude of the Doppler shift is greater than that of a heart beat or the movement of a maternal blood vessel.

In another embodiment, the method further comprises the step of constructing a feature vector for each of the timeframes. The classification is assigned using a pattern recognition module that recognizes a classification for each feature vector. A feature vector is a collection of data which is used by a pattern recognition module as input. For image processing a feature vector would likely be the pixel values in an image. For this application, the ultrasound data is processed. For instance a fast Fourier transform, a wavelet transform, a Wigner distribution, or the power density are extracted. These quantities can be calculated as a function of the velocity or frequency at which is generating the Doppler shift. This embodiment is advantageous, because a pattern recognition module can be used to identify what is happening in each of the timeframes using the feature vector as input. The pattern recognition module can be a trained software module that is trained using training data. This can be simulated ultrasound data used to generate simulated feature vectors for the training, or actual data acquired using an ultrasound system can be used as input. Once a classification has been determined for each of the timeframes, the anatomical structure causing the Doppler shifts can be determined using these classifications. For the example of recognizing a fetal heart, this works well because when a particular state of the fetal heart is determined other events have a high probability of occurring afterwards. What is meant by this is that there is a regular sequence of the heart valves closing and the chambers of the heart pumping. The pattern recognition module can be trained to recognize these patterns. The pattern recognition module used to assign the classification and to recognize the anatomical structure using the classifications may be a single software module or it may be comprised of multiple software modules. In other words, a different pattern recognition method may be used for assigning the classifications and for recognizing the anatomical structure.

In another embodiment, the pattern recognition module is further adapted for recognizing different types of fetal body motion using the feature vector. Different types of fetal body motion can be classified for instance motion of the fetus, hiccupping, and sneezing can be determined. Fetal body motion is very slow in comparison to heart valve motion and to heart wall motion. As a result the lower frequency movements show up at a lower frequency in a Fourier transform. A pattern recognition module can be used to identify these fetal body motions also. This is beneficial, because it allows physicians to not only know the heart rate of the fetus, but to know what sort of motion or motions the fetus is going through. This is very useful for establishing the health of the fetus and if the fetus is alive or not.

In another embodiment the method further comprises the step of receiving a measurement from a labor contraction sensor. The feature vector then comprises the measurement from the labor contraction sensor. This is an extremely beneficial embodiment, because the measurement of the maternal contractions using the labor contraction sensor can be incorporated into the model of the fetal heart rate. During contractions the fetal heart rate changes. Having data from the labor contraction sensor included in the feature vector and included in the model used by the pattern recognition module increases the accuracy of quickly identifying if the fetal heart rate is being measured and also in determining the fetal heart rate. The fetal heart rate during the contractions is also of concern to physicians. Having this information correlated allows physicians to make better diagnostic decisions on the delivery of the fetus.

In another embodiment, the method further comprises the step of receiving a phono cardiography measurement from a microphone. The method further comprises the step of constructing the feature vector using the phono cardiography measurement from the microphone. A phono cardiography measurement is the measurement of a fetal heart using a microphone. This provides complementary information which could be included in the feature vector and would assist the pattern recognition module in properly indentifying if an ultrasound transducer is properly placed over a fetal heart.

The system used to make the phonocardiography measurement may have a noise cancellation sub system.

In another embodiment, the method further comprises: receiving a measurement from a electrocardiography system and constructing the feature vector using the measurement from the electrocardiography system.

In another embodiment, the method further comprises: receiving a measurement from a pulse oximetry system and constructing the feature vector using the measurement from the pulse oximetry system.

In another embodiment, the method further comprises: receiving a measurement from a saturation of peripheral oxygen system and constructing the feature vector using the measurement from the saturation of peripheral oxygen system.

In another embodiment, the method further comprises: receiving a measurement from a non-invasive blood pressure system and constructing the feature vector using the measurement from the saturation of non-invasive blood pressure system.

In another embodiment, the pattern recognition module is an implementation of a hidden Markov model. This is a very advantageous embodiment, because hidden Markov models look at individual pieces of sequential data. In this case timeframes are being examined. The hidden Markov model uses the probability that other events will follow. This method allows very accurate and robust models to be constructed which can identify the fetal heart rate.

In another embodiment, the method further comprises the step of pre-processing the ultrasound data. The step of pre-processing the ultrasound data comprises at least one of the following: filtering the ultrasound data, amplifying the ultrasound data and normalizing the ultrasound data. This is useful, because the filtering process can remove unwanted noise from the ultrasound data, amplifying the ultrasound data can enlarge weak signals and normalizing the ultrasound data reduces the dynamic range and allows for more easy analysis using the pattern recognition module.

In another aspect, embodiments of the invention provide for a computer program product comprising machine executable instructions for execution by a control system. The machine executable instructions comprise an embodiment of a method of determining a fetal heart rate.

In another aspect, embodiments of the invention provide for a computer program product comprising machine executable instructions for execution by a control system. The machine executable instruction comprises the step of receiving ultrasound data. The ultrasound data comprises Doppler shift information is descriptive of the the velocity of the at least one anatomical structure. The instructions further comprise the step of dividing the ultrasound data into a series of time frames. The instructions further comprise the step of assigning each of the time frames a classification using the Doppler shift information. The instructions further comprise the step of recognizing the at least one anatomical structure using the classification of each time frame. The advantages of this have been previously discussed.

In another aspect, the invention provides for a control system comprising a microprocessor wherein the microprocessor is adapted for performing the step of receiving ultrasound data. The ultrasound data comprises Doppler shift information is descriptive of the the velocity of the at least one anatomical structure. The instructions further comprise the step of dividing the ultrasound data into a series of time frames. The instructions further comprise the step of assigning each of the time frames a classification using the Doppler shift information. The instructions further comprise the step of recognizing the at least one anatomical structure using the classification of each time frame. The advantages of this have been previously discussed.

In another embodiment, the step of assigning each sequential time frame a classification using the Doppler shift information comprises the step of identifying fetal heart valve motion data using the Doppler shift information. The step of assigning each sequential time frame a classification using the Doppler shift information further comprise the step of identifying fetal heart wall motion data using the Doppler shift information. A fetal heart is then recognized as being an anatomical structure using the classification of each of the time frames.

In another embodiment, the fetal heart valve motion data is identified using a high-pass filter on the ultrasound data and wherein the fetal heart wall motion data is identified using a low-pass filter. This is advantageous, because as it was previously mentioned the heart valve motion is more rapid than the heart wall motion. In a Fourier transform and in other single processing techniques the heart wall motion will show up as being lower frequency than the fast moving heart valve motion data. The high-pass and low-pass filter can be implemented digitally. In other embodiments, analogue high-pass and low-pass filters can also be used.

In another embodiment the high-pass filter uses a cut-off frequency between 200 and 400 Hz. Preferably the high-pass filter uses a cut-off frequency between 250 and 350 Hz. The optimum cut-off frequency is approximately 300 Hz. In another embodiment, the low-pass filter uses a cut-off frequency between 200 and 400 Hz. The low-pass filter preferably uses a cut-off frequency between 250 and 350 Hz. Again the optimum cut-off frequency for the low-pass filter is approximately 300 Hz.

In another embodiment, the step of assigning each time frame a classification using the Doppler shift information comprise the step of identifying fetal body motion data using the Doppler shift information. The anatomical structure is then identified to be a fetal body using the classification of each of the time frames.

In another embodiment, fetal body motion is identified using a low pass filter with a cutoff ferequency between 1 Hz and 15 Hz. The cutoff frequency is optimally between 8 and 12 Hz.

In another aspect, the invention provides for a fetal monitor. The fetal monitor comprises an ultrasound system adapted for measuring Doppler shifted ultrasound signals using an ultrasonic transducer. The ultrasonic system is adapted for generating ultrasound data using the Doppler shifted ultrasound signals. The fetal monitor further comprises a control system according to an embodiment of the invention.

In another embodiment, the fetal monitor further comprises a labor contraction sensor. The control system is further adapted for performing the step of constructing a feature vector for each of the timeframes and the measurement from the labor contraction sensor. The control system is further adapted for performing the step of classifying the fetal heart motion in each of the timeframes using a pattern recognition module that recognizes the classification for each feature vector. The classification is assigned using a pattern recognition module that recognizes a classification for each feature vector. The anatomical structure is determined using the pattern recognition module. As mentioned previously, the pattern recognition module can be comprised of multiple sub modules, with the sub modules comprising pattern recognition software modules. The advantages of this embodiment have been previously discussed. The fetal heart rate in this embodiment is determined using the classification of the fetal heart motion.

In another embodiment, the fetal monitor is adapted for indicating the at least one anatomical structure on an indicator. The indicator may be a display on the fetal monitor or it may be written onto a chart recorder. This embodiment is beneficial, because it is advantageous to know what anatomical structure is being examined with the fetal monitor. This feature could help prevent errors where the fetal monitor is not examining a fetus.

In another embodiment, the fetal monitor is adapted for warning an operator with an alarm if the at least one anatomical structure does not include a heart. The alarm could be a visual indicator, an audible alarm, or it could be a marking on a chart recorder. This embodiment is beneficial, because the operator will then know that the ultrasound transducer should be repositioned.

In another embodiment, the fetal monitor is adapted for displaying a measure of the confidence that the fetal heart rate is from a fetus on an indicator. Examples of indicators are a display on the fetal monitor, an audible tone, or a marking on a chart recorder. This embodiment is beneficial; because it gives an operator or caregiver an indication of how likely it is that the transducer is positioned correctly. This embodiment can be implemented easily when a pattern recognition module is used. Many pattern recognition modules such as HMMs also generate a possibility that the pattern is recognized correctly. This probability could be used to generate the measure of confidence. The fetal heart rate may be displayed on a numerical indicator on the fetal monitor, it may be indicated audibly, it may also be recorded on a chart recorder and it may be send to an electronic recording system.

BRIEF DESCRIPTION OF THE DRAWINGS

In the following preferred embodiments of the invention will be described, by way of example only, and with reference to the drawings in which.

DETAILED DESCRIPTION OF EMBODIMENTS

Like numbered elements in these figures are either identical elements or perform the same function. Elements which have been discussed previously will not necessarily be discussed in later figures if the function is identical.

Figure 1:
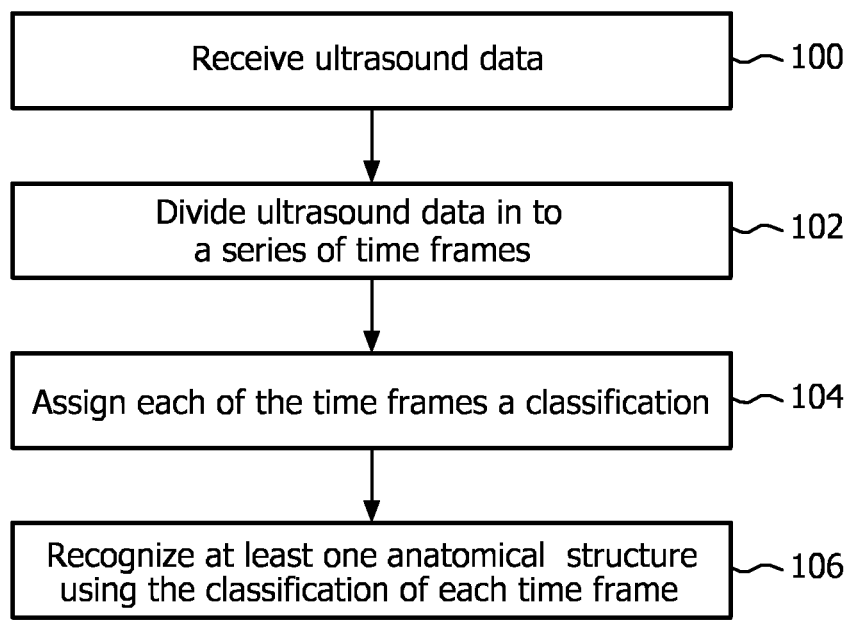
FIG. 1 shows an embodiment of a method of determining an anatomical structure using Doppler shifted ultrasound data.

FIG. 1 shows a method of recognizing an anatomical that is generating Doppler shift information in ultrasound data. In step 100 ultrasound data is received. In step 102 the ultrasound is divided into a series of time frames. Next, in step 104, each of the time frames is assigned a classification. In step 106, at least one anatomical structure is recognized using the classification of each time frame. The movements of different anatomical structures produce different types of Doppler shifts in the ultrasound data. For instance, the movement of a fetal heart contains several different components. There is a fast moving heart valve and a slower moving heart wall. The heart walls and valves move in a rhythmic fashion that can be recognized and used to confirm that the ultrasound sensor is positioned over a fetal heart.

Once it is known that the ultrasound sensor is positioned over a fetal heart, The fetal heart valve motion and the fetal heart wall motion can be used to directly determine the fetal heart rate, or the fetal heart valve motion and the fetal heart wall motion can be used to confirm that the sensor is indeed measuring a fetal heart rate. Once the measurement of a fetal heart has been confirmed, then a conventional method can be used for determining the fetal heart rate.

Figure 2:
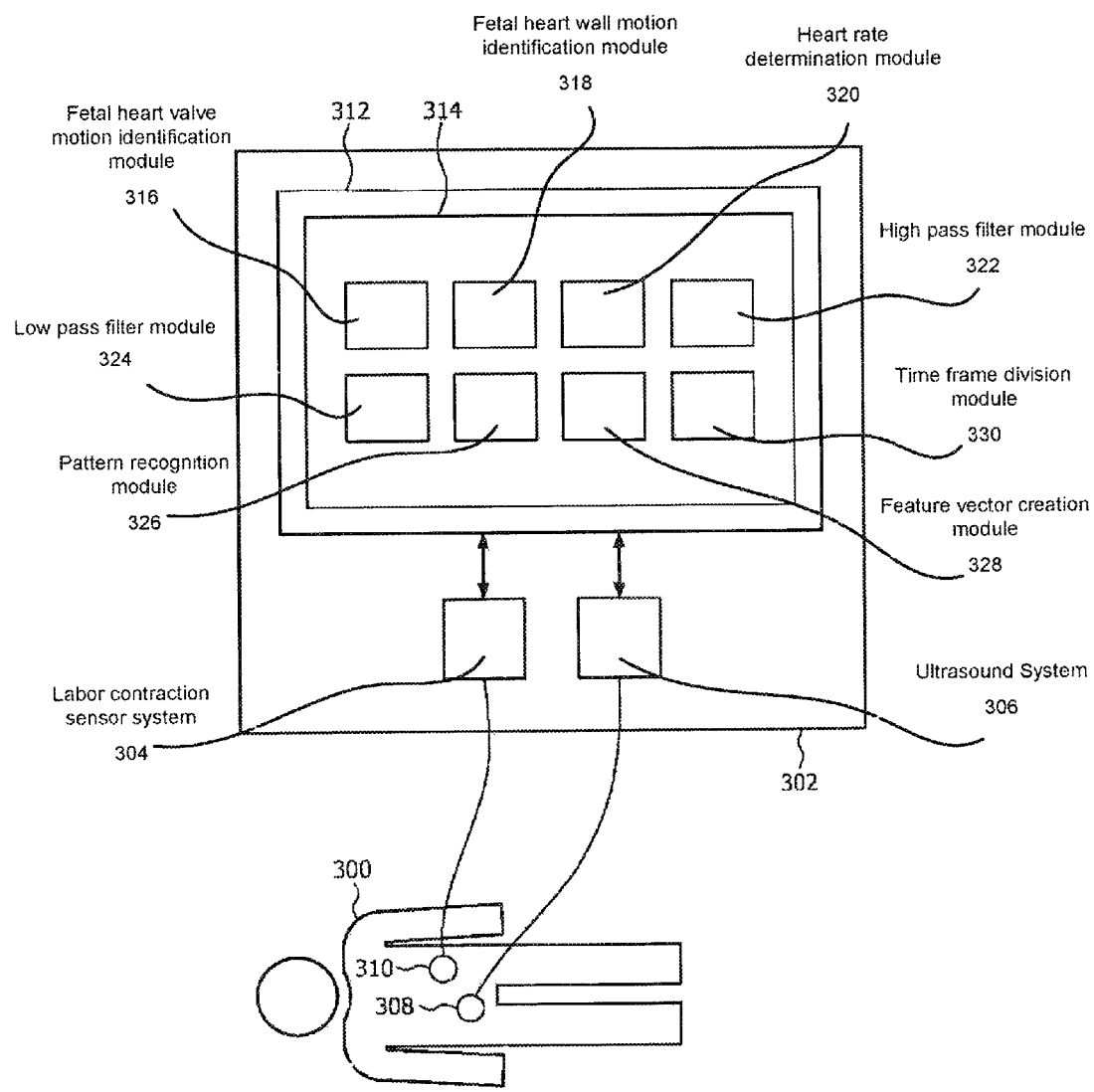
FIG. 2 shows an embodiment of a fetal monitor according to an embodiment of the invention.

FIG. 2 shows an embodiment of a fetal monitor 302 according to an embodiment of the invention. Shown is a pregnant subject 300. The pregnant subject 300 has a labor contraction sensor 310 and an ultrasound transducer 308 on her abdomen region. The labor contraction sensor is attached to a labor contraction sensor system 304. The labor contraction sensor system 304 is the electronics necessary for running the labor contraction sensor 310. The labor contraction sensor system 304 interfaces with a microprocessor 312. The ultrasound transducer 308 is attached to an ultrasound system 306. The ultrasound system 306 comprises the electronics necessary for driving and operating the ultrasound transducer 308. The ultrasound system 306 is connected to the microprocessor 312. The microprocessor 312 functions by executing a computer program product 314. The computer program product 314 operates and performs the method of determining the fetal monitor. The computer program product 314 comprises a number of different software modules. Module 316 is a fetal heart valve motion identification module. Module 318 is a fetal heart wall motion identification module. Module 320 is a heart rate determination module. 322 is an implementation of a digital high-pass filter module. Module 324 is an implementation of a digital low-pass filter module. 326 is a pattern recognition module. The pattern recognition 326 may be a trained software module that may also include a library of training data used to compare against, or may also contain a database of examples to reference against when it operates. Module 328 is a feature vector creation module. And module 330 is a software module which divides the ultrasound data into a series of timeframes. The microprocessor 312 receives the ultrasound data from the ultrasound system 306.

Figure 3:
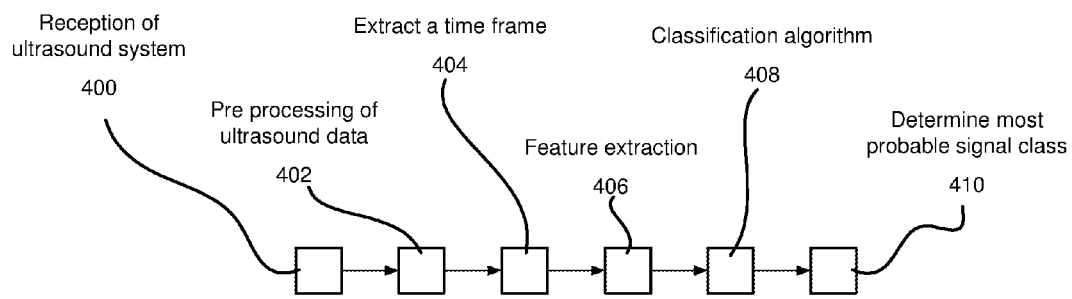
FIG. 3 shows a further embodiment of a method according to the invention.

FIG. 3 shows a block diagram of a method according to an embodiment of the invention. In step 400 an ultrasound signal is received. In step 402 the ultrasound signal is pre-processed. Next in step 404 a timeframe is extracted. The ultrasound signal or ultrasound data is chopped into tiny pieces and one or more timeframes are extracted. In step 406 feature extraction is performed, in this step feature vectors are created for each of the timeframes that were extracted. In step 408 each feature vector is sent to a classification algorithm. The classification algorithm may be a pattern recognition module. The classification or pattern recognition module identifies each feature vector for one of a variety of different states for instance the timeframe may identify that the heart valves are moving, it may identify that the heart walls or moving, or it may identify that neither the heart valves or the heart wall are moving. In step 410 the classification algorithm outputs the most probable signal class.

The input signal for the new pattern recognition module is a standard ultrasonic signal (see FIG. 3). At first, the data is preprocessed: It is filtered, amplified, and normalized to fulfill the needs for further processing. Then time frames that are much shorter than on heart beat are extracted from the data. For every time frame, certain criteria (e.g. the results of FFT, wavelet transformations, Wigner distribution, or the power density) are extracted. Together, these criteria build up a feature vector that contains significant attributes of the current time frame. All feature vectors are sent into a signal classifier (for details see FIG. 4), that compares the feature vectors in view of their sequence and occurrence to pre-defined HMMs of fetal or maternal signal sources. The outputs of the signal classification are the probabilities for the correlation of the current ultrasound pattern with one of the predefined ultrasonic pattern models. The HMM that produces the highest probability for the current ultrasound pattern describes the current physiological signal source. Furthermore, those probabilities are an indicator for the current signal quality. If all probabilities are low, the signal is weak and a warning can be signaled to the caregiver to replace the sensor.

Figure 4:
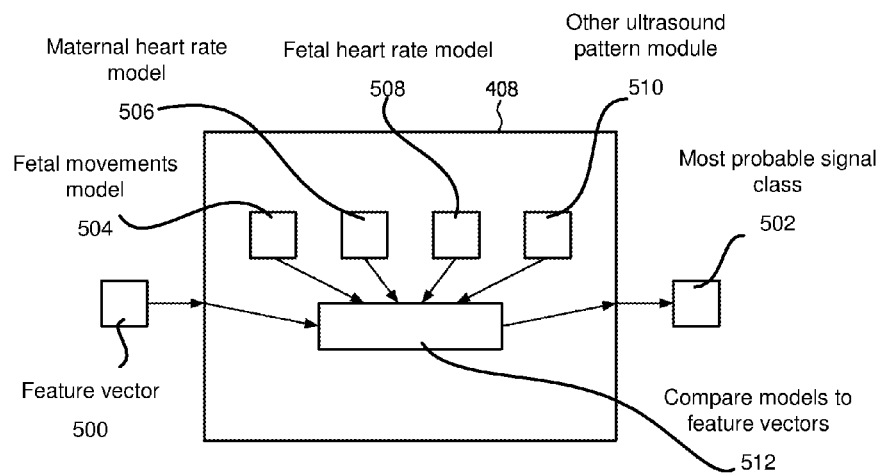
FIG. 4 shows an example of a classification algorithm according to an embodiment of the invention.

FIG. 4 shows a diagram illustrating the operation of the classification algorithm 408. The classification algorithm 408 receives a feature vector 500 or feature vectors 500 as input. The classification algorithm 408 then outputs a most probable signal class 502. In this example the signal class can be identified as to the probability that it is a fetal movement, a maternal heart rate, a fetal heart rate, or other ultrasound pattern. There is a module 512 which compares the feature vector to a variety of ultrasound models. The models which the comparison algorithm 512 can compare against in this example are a fetal movement model 504, a maternal heart rate model 506, a fetal heart rate model 508, and another ultrasound pattern module 510. The algorithm in plot 512 can be implemented using a hidden Markov algorithm.

Figure 5:
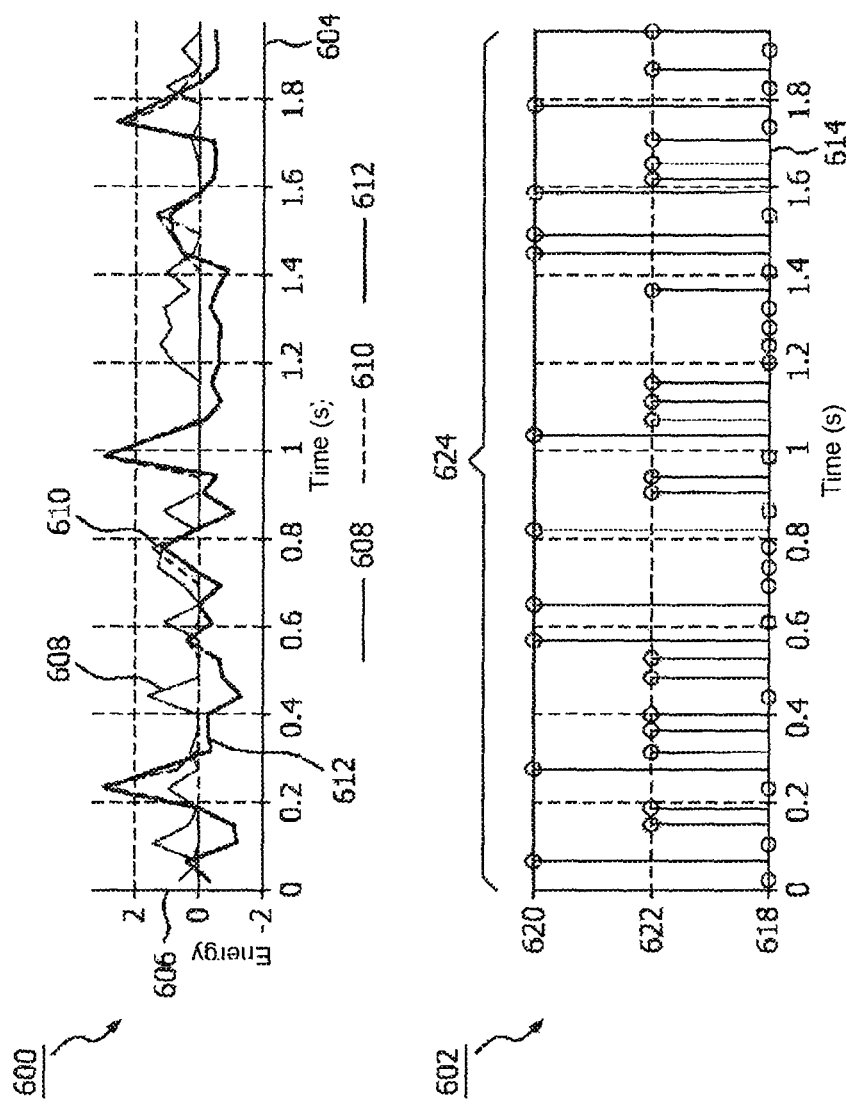
FIG. 5 shows infant ultrasound data processed by high and low pass filters and a classification of different time frames by a Hidden Markov Model.

FIG. 5 shows a plot of the power of different frequency ranges in ultrasound data 600 and example of hidden Markov model classifying the different motions of a fetal heart 602. In FIG. 600, the time is access 604 and the energy in the frequency range is given on access 606. The energy range on access 606 is in arbitrary units. Curve 608 shows the energy in the high band as determined by a high-pass filter. 610 determines the energy in a low band as determined by a low-pass filter. And curve 612 is a ratio of curve 608 to curve 610. In plot 602 markers 624 within the plot indicate the heart motion as determined by hidden Markov model. Access 614 is the time in seconds and there are three positions in the plot labeled 620, 622 and 618. 620 indicates that heart wall motion is identified, 622 indicates that neither a heart valve nor a heart wall motion is identified or is a pause time and 618 indicates that a heart valve motion has been detected. Plot 602 is an example of how data could be identified using a hidden Markov model. This can also be used as a model which can be compared against to determine if a fetal heart rate is detected or not.

For the example shown in FIG. 5, a FM 30 fetal monitor was used. To calculate curve 608, the power in the high band (300 Hz to 600 Hz) of a short-time Fourier transform (STFT) of the Doppler shift ultrasound data was taken. Curve 608 was normalized by subtracting the average energy in the high band and then dividing by the square root of the variance of the energy in the high band. To calculated curve 610, the power in the low band (0 Hz to 300 Hz) was taken using a STFT also. Similarly, the curve 610 was normalized by subtracting the average energy in the low band and dividing by the square root of the variance of the energy in the low band.

LIST OF REFERENCE NUMERALS

300 Pregnant subject
302 Fetal monitor

304 Labor contraction sensor system
306 Ultrasound system
308 Ultrasound transducer
310 Labor contraction sensor
312 Microprocessor
314 Computer program product
316 Fetal heart valve motion identification module
318 Fetal heart wall motion identification module
320 Heart rate determination module
322 High pass filter module
324 Low pass filter module
326 pattern recognition module
328 Feature vector creation module
330 Time frame division module
400 Reception of ultrasound system
402 Pre processing of ultrasound data
404 Extract a time frame
406 Feature extraction
408 Classification algorithm
410 Determine most probably signal class
500 Feature vector
502 Most probably signal class
504 Fetal movements model
506 Maternal heart rate model
508 Fetal heart rate model
510 Other ultrasound pattern module
512 Compare models to feature vector
600 Power of different frequency ranges in ultrasound data
602 Example of hidden markov model of fetal heart.
604 Time in seconds
606 Energy in arbitrary units
608 Energy in high band
610 Energy in low band
612 Ratio of 608 to 610
614 Time in seconds
618 Heart valve
620 Heart wall
622 Pause
624 Indication of heart activity

The invention claimed is:

1. A method of recognizing at least one moving fetal anatomical structure using ultrasound data, the method comprising:
   receiving, by a processor of a fetal monitor, the ultrasound data, wherein the ultrasound data comprises Doppler shift information descriptive of the velocity of the at least one moving fetal anatomical structure,
   dividing, by the processor, the ultrasound data into a series of time frames, determining a feature vector for each of the time frames, wherein each feature vector represents a component of the at least one moving fetal anatomical structure,
   assigning, by the processor, each of the time frames a classification using the Doppler shift information, the classification being assigned using a pattern recognition module of the processor that determines the classification based on the respective feature vector of the time frame being assigned, the classification being indicative of a movement state of each of the at least one moving fetal anatomical structure, and
   recognizing, by the pattern recognition module of the processor, the at least one moving fetal anatomical structure using patterns derived from the classification of each time frame.

2. The method of claim 1, wherein the assigning each of the time frames a classification using the Doppler shift information comprises:
   identifying fetal heart valve motion data using the Doppler shift information,
   identifying fetal heart wall motion data using the Doppler shift information, and
   wherein a fetal heart is recognized as the at least one moving fetal anatomical structure.

3. The method of claim 1, wherein assigning each of the time frames a classification using the Doppler shift information further comprises:
   identifying fetal body motion using the Doppler shift information, and wherein the at least one moving fetal anatomical structure is identified to be a fetal body using the classification of each of the time frames.

4. The method of claim 1, wherein the pattern recognition module is further adapted for recognizing different types of fetal body motion using the feature vector.

5. The method claim 1, wherein the method further comprises:
   receiving a measurement from a labor contraction sensor and constructing each feature vector using the measurement from the labor contraction sensor,
   wherein the method further comprises receiving a phono cardiography measurement from a microphone and constructing each feature vector using the phono cardiography measurement from the microphone,
   wherein the method further comprises receiving a measurement from a electrocardiography system and constructs each feature vector using the measurement from the electrocardiography system,
   wherein the method further comprises receiving a measurement from a pulse oximetry system and constructs each feature vector using the measurement from the pulse oximetry system,
   wherein the method further comprises receiving a measurement from a saturation of peripheral oxygen system and constructs each feature vector using the measurement from the saturation of the peripheral oxygen system,
   wherein the method further comprises receiving a measurement from a non-invasive blood pressure system and constructs each feature vector using the measurement from the non-invasive blood pressure system.

6. The method of claim 1, wherein the pattern recognition module is an implementation of a hidden Markov model.

7. A non-transitory computer-readable medium carrying software comprising machine executable instructions for execution by a control system, the machine executable instructions comprising the steps of:
   receiving ultrasound data, wherein the ultrasound data comprises Doppler shift information descriptive of the velocity of at least one moving fetal anatomical structure,
   dividing the ultrasound data into a series of time frames,
   determining a feature vector for each of the time frames, wherein each feature vector represents a component of the at least one moving fetal anatomical structure,
   assigning each of the time frames a classification using the Doppler shift information, the classification being assigned using a pattern recognition module that determines the classification based on the respective feature vector of the time frame being assigned, the classification being indicative of a movement state of each of the at least one moving fetal anatomical structure, and recognizing the at least one moving fetal anatomical structure using patterns derived from the classification of each time frame.

8. A control system, comprising:

a microprocessor configured to perform the steps of:

receiving ultrasound data, wherein the ultrasound data comprises Doppler shift information descriptive of the velocity of at least one moving fetal anatomical structure, dividing the ultrasound data into a series of time frames, determining a feature vector for each of the time frames, wherein each feature vector represents a component of the at least one moving fetal anatomical structure, assigning each of the time frames a classification using the Doppler shift information, the classification being assigned using a pattern recognition module that determines the classification based on the respective feature vector of the time frame being assigned, the classification being indicative of a movement state of each of the at least one moving fetal anatomical structure, and recognizing the at least one moving fetal anatomical structure using patterns derived from the classification of each time frame; and a memory arrangement configured to store the ultrasound data.

9. The control system of claim 8, wherein assigning each time frame a classification using the Doppler shift information further comprises the steps of:

identifying fetal heart valve motion data using the Doppler shift information, identifying fetal heart wall motion data using the Doppler shift information, and wherein a fetal heart is recognized as the at least one moving fetal anatomical structure using the classification.

10. The control system of claim 9, wherein the fetal heart valve motion data is identified using a high pass filter on the ultrasound data, wherein the fetal heart wall motion data is identified using a low pass filter, wherein the high pass filter uses a cutoff frequency between 200 Hz and 400 Hz, and wherein the low pass filter uses a cutoff frequency between 200 Hz and 400 Hz.

11. The control system of claim 10, wherein the high pass filter uses a cutoff frequency between 250 Hz and 350 Hz and wherein the low pass filter uses a cutoff frequency between 250 Hz and 350 Hz.

12. The control system of claim 9, wherein assigning each time frame a classification using the Doppler shift information comprises the steps of:

identifying fetal body motion data using the Doppler shift information, and wherein the at least one moving fetal anatomical structure is identified to be a fetal body using the classification of each of the time frames, and wherein the fetal body motion data is identified using a low pass filter with a cutoff frequency between 1 Hz and 15 Hz.

13. The control system of claim 12, wherein the cutoff frequency is between 8 Hz and 12 Hz.

14. The control system of claim 8 further comprising an ultrasound system adapted for measuring Doppler shifted ultrasound signals using an ultrasonic transducer, wherein the ultrasound system is adapted for generating the ultrasound data using the Doppler shifted ultrasound signals.

15. The control system of claim 14, further comprising a labor contraction sensor, wherein the microprocessor is further programmed for performing the steps of:

constructing the feature vector for each of the time frames using a measurement from the labor contraction sensor.

16. The control system of claim 14, wherein the microprocessor is adapted for indicating the at least one moving fetal anatomical structure on an indicator, wherein the microprocessor is adapted for warning an operator with an alarm if the recognized at least one moving fetal anatomical structure does not include a fetal heart, and further comprising a display for displaying a fetal heart rate and a measure of a confidence that the fetal heart rate is from a fetus.

* * * * *